United States Patent [19]
Young

[11] Patent Number: 5,234,338
[45] Date of Patent: Aug. 10, 1993

[54] AUTOCLAVABLE HEAD AND HANDLE FOR DENTAL SYRINGE

[75] Inventor: Barry S. Young, Tualatin, Oreg.

[73] Assignee: DCI International, Inc., Newberg, Oreg.

[21] Appl. No.: 861,648

[22] Filed: Apr. 1, 1992

[51] Int. Cl.⁵ .................................................. A61G 17/02
[52] U.S. Cl. ................................................ 433/80; 433/126
[58] Field of Search .................................... 433/80, 126

[56] References Cited

U.S. PATENT DOCUMENTS

| | | | |
|---|---|---|---|
| 3,698,088 | 10/1972 | Austin, Jr. | 433/80 |
| 4,249,899 | 2/1981 | Davis | 433/80 |
| 4,619,612 | 10/1986 | Weber et al. | 433/80 |
| 4,950,159 | 8/1990 | Hansen | 433/80 |

Primary Examiner—John J. Wilson
Attorney, Agent, or Firm—Trask, Britt & Rossa

[57] ABSTRACT

A dental syringe is constructed as an assembly of which the handle, head and tip components, which together include substantially all of the exterior surfaces of the syringe, can be quickly detached from an internal cartridge, which is connected to the utility conduits. The cartridge is constructed to close off the utility lines when it is detached from and to open the utility lines when it is connected to the remainder of the assembly.

24 Claims, 4 Drawing Sheets

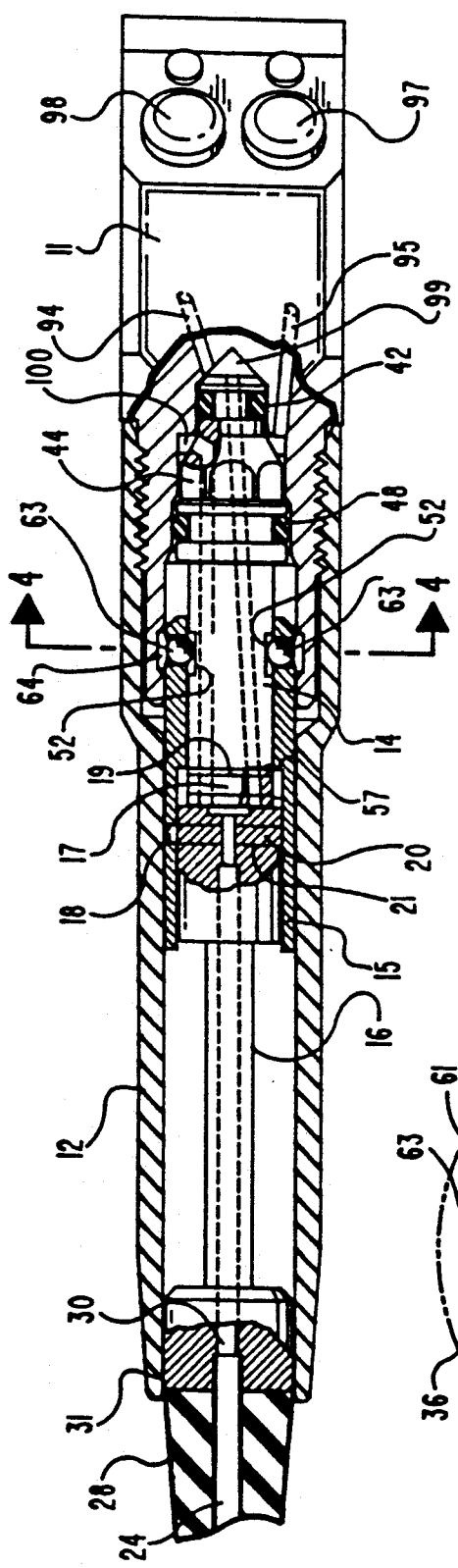
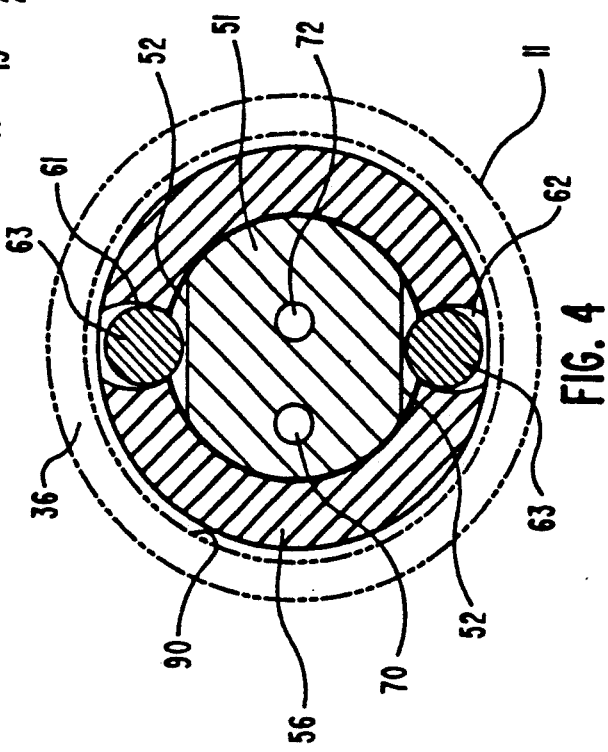
FIG. 3
FIG. 4

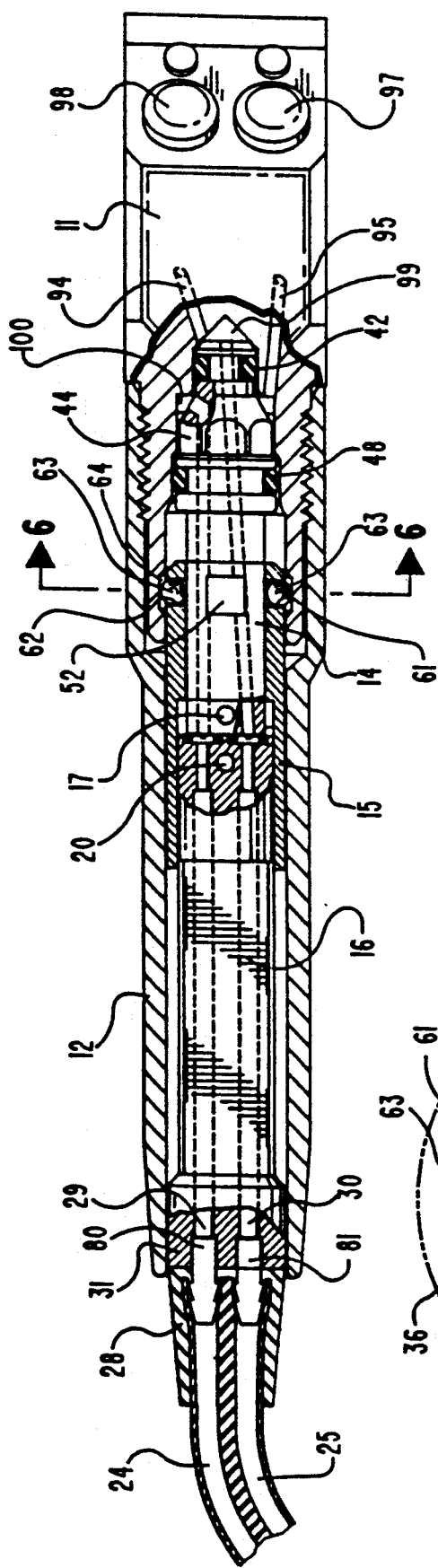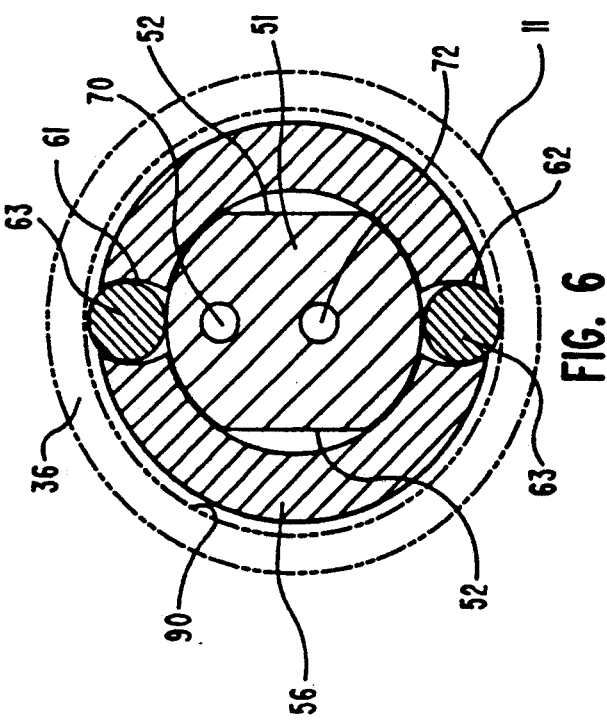

AUTOCLAVABLE HEAD AND HANDLE FOR DENTAL SYRINGE

BACKGROUND OF THE INVENTION

1. Field

The present invention relates to dental syringes, and more particularly to dental syringes that may be easily disconnected from tubing supplying utilities to the syringe so that contaminated portions of the syringe may be sterilized.

2. State of the Art

Dental syringes are widely used by dentists, dental hygienists, dental assistants and the like. They are hand-held instruments which deliver water and air under pressure into a patient's mouth for washing and drying purposes. Commonly, air is supplied to the dental syringe and into the patient's mouth at about 80 psi, and water is supplied at about 40 psi. One such dental syringe is disclosed in U.S. Pat. No. 3,698,088. This patent discloses a syringe having a head, which is coupled to utility supply hoses, and an elongate tip, which is coupled to the head and is inserted into the patient's mouth. Valves in the head are selectively hand operated to discharge water or air through the distal end of the tip.

Cross-contamination of one patient by another is one of the principle problems encountered with the use of dental syringes. Bacteria and viruses can be communicated from patient to patient unless the components of the syringe are adequately sanitized. U.S. Pat. No. 4,248,589 discloses a dental syringe assembly which has a quickly and easily removed syringe tip. The '589 patent discloses that the syringe tip can be readily removed from the head and autoclaved after each patient treatment. It is also noted that with the quick disconnect tip arrangement of the patent, worn tips or tips of different configurations can quickly and easily be replaced or substituted for use with the head.

Sterilized syringe tips, while proving safer and better received than tips which have not been sterilized are still inadequate for current conditions.

The widespread occurrence of the HIV virus has come to be recognized by the public generally. The recognition that the HIV virus, as well as other bacteria and viruses, may be transmitted during dental procedures has incentivized the dental profession and dental patients to demand further improvements in the general cleanliness and sanitation levels maintained in dental operatories. It is thus of increasing importance that the equipment used by dentists be constructed so that contaminated surfaces may be quickly and easily sanitized. A presently preferred and effective method of sanitization of such equipment is autoclaving. Autoclaving and other sterilization procedures must typically be effected in special equipment remote from the utility supply lines.

While others have proposed the use of dental equipment having quick disconnect couplings so that the equipment, i.e. dental handpieces and dental syringes, can be quickly and easily disconnected and transported to be autoclaved, the structures proposed have not allowed full autoclave treatment to the entire dental syringe, handpiece, or other item of dental equipment. Generally, the presently available such equipment requires that a large segment of a handle component remain always in attachment with the utility supply conduits (hoses or tubing). The reason for this design constraint is that means must be provided for isolating the utilities when an equipment item is removed to be autoclaved. It has been considered necessary for the component attached to the supply conduits to include control valves as necessary to shut off utility flow through the tubing. As a practical consequence, portions of the exterior surfaces of necessary dental operatory equipment cannot be autoclaved or otherwise sterilized. These surfaces are subject to contamination, and continue to present a hazard to dental patients and practitioners.

There remains a need for a dental syringe assembly constructed so that its entire external surface, including its entire handle, can be easily and quickly disconnected from its utility connections without releasing any appreciable amount of utility into the ambient region. Such an arrangement would permit the remote sterilization, notably autoclaving, of the entire external surface of the syringe.

SUMMARY OF THE INVENTION

The present invention provides a dental syringe assembly in which the entire external housing, including the handle, is quickly and easily removed from attachment to the utility supply lines, so that all of the external surfaces of the housing may be autoclaved.

The dental syringe of this invention includes a substantially internal quick-disconnect mechanism wherein flow of air and water is discontinued in response to a manipulation, such as a simple turning motion, incidental to separating the external portion of the syringe assembly from its associated utility (typically air and water) supply conduits (typically flexible tubing).

Typical embodiments of the invention provide a dental syringe having a head with a removable tip, and a handle projecting from the head. These elements include substantially all of the exterior surfaces of the syringe assembly which are exposed to contamination in a dental operatory. An attachment cartridge is secured to the discharge ends of air and water tubing, and constitutes a first portion of an internal quick disconnect mechanism. This cartridge incorporates a means for attaching to a second portion of the quick disconnect mechanism residing within the handle (and/or head) of the syringe. The quick disconnect mechanism also constitutes means for permitting or discontinuing air and water flow into the syringe head.

The attachment cartridge generally comprises a stem, a locking sleeve and a terminal portion. These components interact with corresponding components carried within the assembly.

BRIEF DESCRIPTION OF THE DRAWINGS

In the drawings, which illustrate what is currently regarded as the best mode for carrying out the invention:

FIGS. 2A and 2B are enlarged cross-sectional fragmentary views, taken at the reference lines 2A—2A and 2B—2B, respectively, of FIG. 2;

FIG. 3 is a view like that of FIG. 2, but with the components assembled and the syringe handle shown partially broken away;

FIG. 4 is an enlarged transverse section, taken on the line 4—4 of FIG. 3;

FIG. 5 is a view like that of FIG. 3, but with the attachment cartridge rotated ninety degrees with respect to the syringe head; and FIG. 6 is an enlarged transverse section, taken on the line 6—6 of FIG. 5.

DETAILED DESCRIPTION OF THE ILLUSTRATED EMBODIMENT

Figure 1:
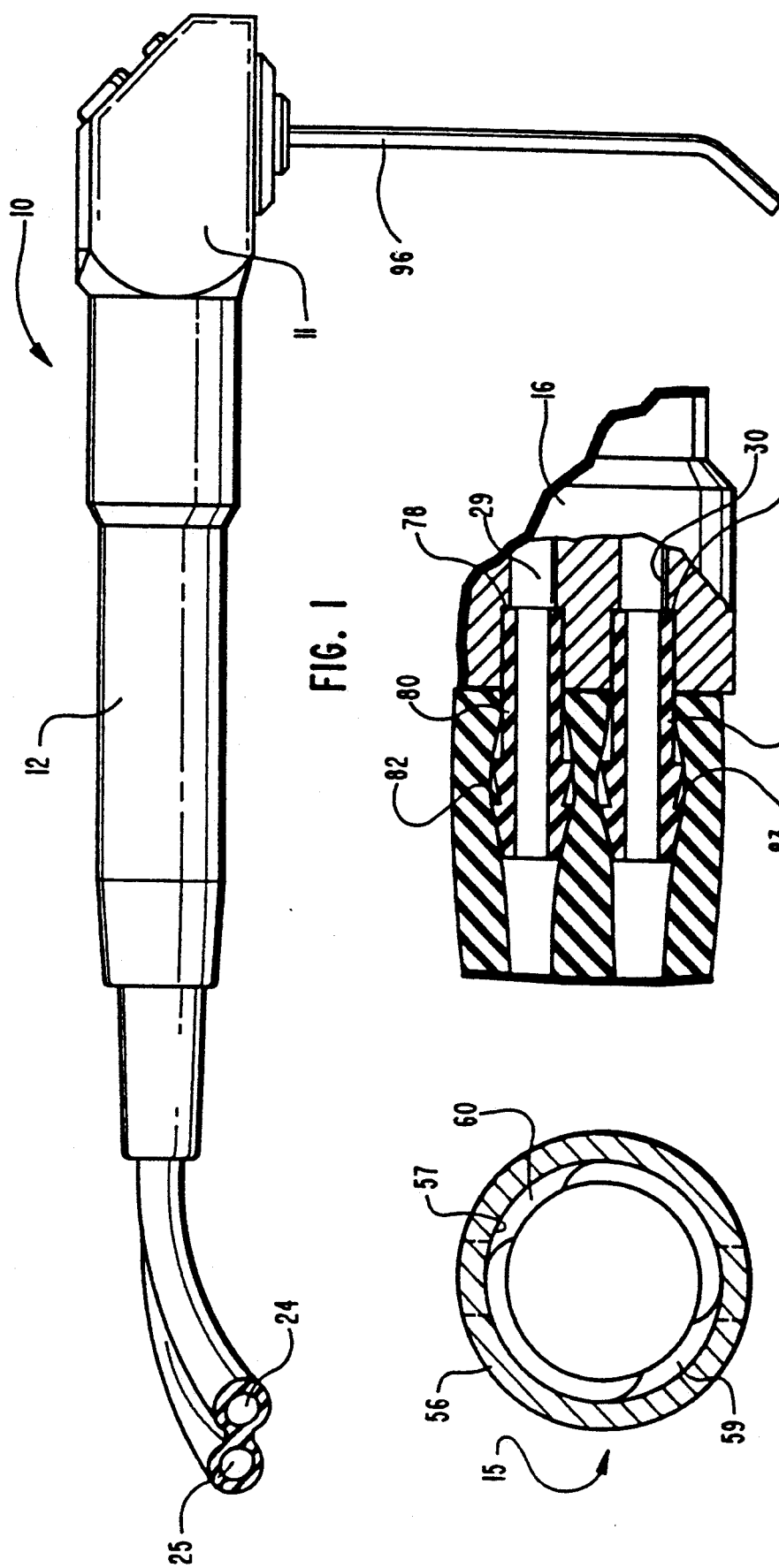
FIG. 1 is a side elevation view of a typical syringe assembly of the invention, including fragments of air and water utility supply tubing.

The syringe assembly of the present invention is shown in FIG. 1 generally at 10. Syringe 10 includes a head 11, a handle 12, and an attachment cartridge shown generally at 13 (FIG. 2) and including a stem portion 14, a locking sleeve 15 and a terminal portion 16.

The stem portion 14 telescopes into the locking sleeve 15 so that a short pin 17 can be inserted fully through a first hole 18 in the locking sleeve 15 and into and through a hole 19 in the stem portion 14 such that the ends of the pin 17 project from opposite ends of hole 19. Terminal portion 16 is also telescoped into locking sleeve 15 and into an abutting, end-to-end relationship with the stem portion 14. A long pin 20 is then inserted through the first hole 18 of the locking sleeve and a hole 21 through the terminal portion 16. The pin 20 also extends through a second hole 18 that is opposite the first hole 18 in the locking sleeve 15. The stem portion 14, locking sleeve 15, and terminal portion 16, when interlocked by the pins 17 and 20, comprise the attachment cartridge 13 that is secured to respective ends of an air tube 24 and a water tube 25.

The tubes 24 and 25 pass tightly through passages 26 and 27, respectively, of a finger grip 28, before being connected to the terminal portion 16 of the cartridge 13. The grip 28 functions both to secure the tubes 24 and 25 and as a means for manipulating the cartridge 13. The grip 28 is specifically useful for applying twisting motion to the cartridge 13 and for inserting and removing the cartridge 13 through the bore 31.

Handle 12 has a hollow interior 32, which is flared at region 33 to an enlarged internally threaded portion 34 which mates with threads 35 formed exteriorly of a boss 36 projecting from head 11. The handle 12, rather than being connected by threads to the head 11 as shown, may alternatively be formed integral with the head 11. The two-piece construction illustrated provides better access for maintenance and cleaning of internal components.

The assembled attachment cartridge 13, made up of interlocked stem portion 14, locking sleeve 15, and terminal portion 16, is inserted into and through the hollow interior 32 of handle 12 to extend into and to project from the hollow interior 38 formed in the boss 36 of head 11. A front end 40 of the stem portion 14 extends into a well 41 provided in the head 11. An "O"-ring seal 42 carried within a groove provided in the end 40 of stem 14 engages the wall of well 41 to prevent fluid flow across this interface. End piece 40 is flared at 43 into a distal drive head, illustrated as a hex drive 44, formed on the stem portion 14. The hex drive 44 fits into a corresponding socket, illustrated as a hex broach 45 formed in the interior 38 of the head portion 11 such that the cooperation between the hex drive and the hex broach will prevent rotation of the installed stem 14 portion.

Figure 2:
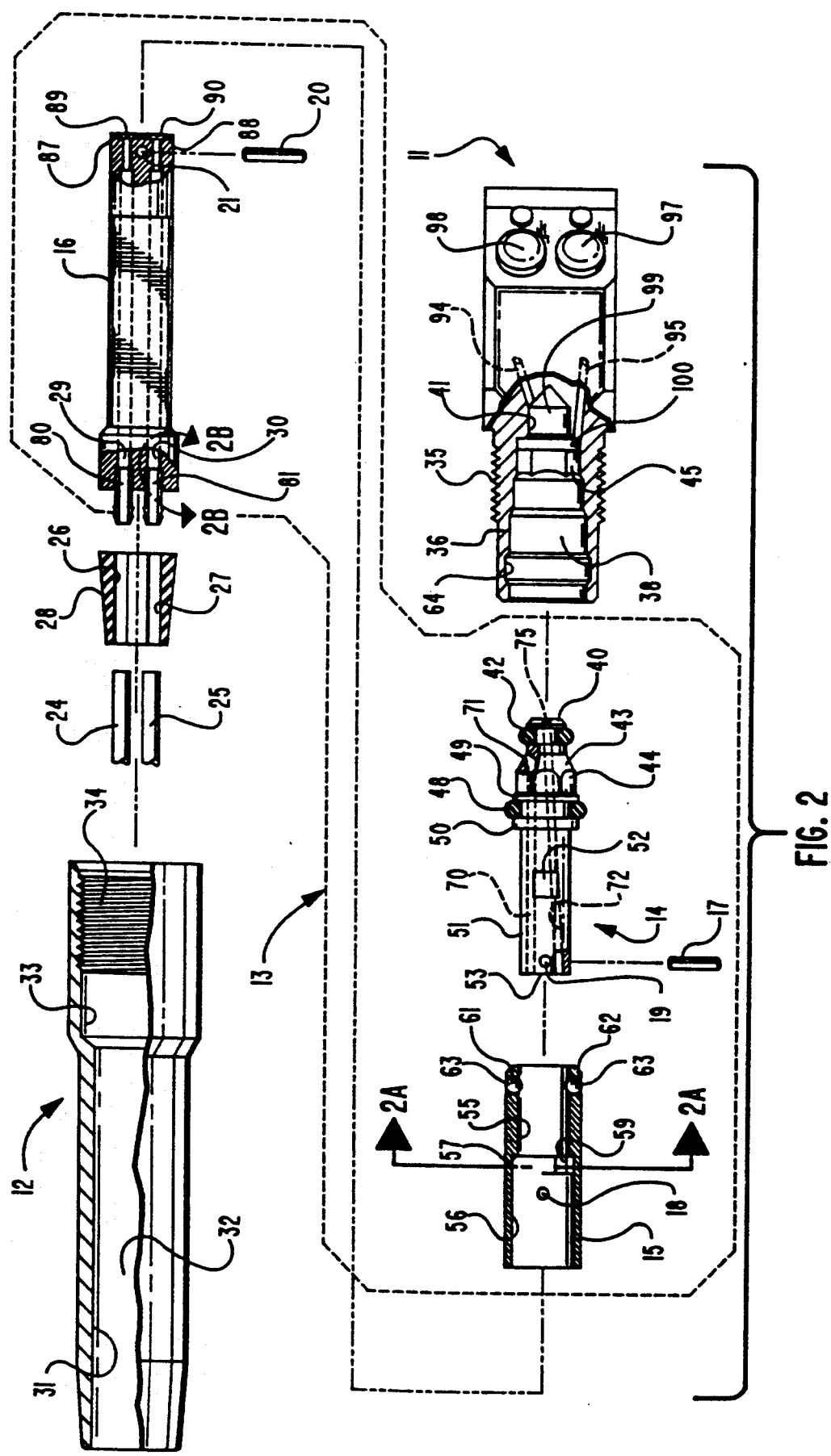
FIG. 2 is an exploded top plan view of the embodiment of FIG. 1, with portions of the various components broken away to show the interiors thereof.

Another "O"-ring 48 is held in place on the stem 14 by a pair of shoulders 49 and 50 (FIG. 2). A shaft 51, with a generally round cross-sectional configuration, extends from the shoulder 50. However, a pair of flat surfaces 52 are formed on respective opposite sides of the shaft 51 intermediate its length, and the hole 19 is formed through the shaft 51 adjacent its free end 53.

The locking sleeve 15 has a smaller diameter hollow interior portion 55 that merges into a larger diameter hollow interior portion 56 through a shoulder 57 located intermediate the length of the locking sleeve 15. Pin stops 59 and 60 (FIG. 2A) are formed on the shoulder 57 such that when pin 17 is fully inserted through the hole 19 (after insertion of the stem portion 14 into the locking sleeve 15), its ends project from opposite sides of the stem portion 14. Rotation and counter-rotation of the locking sleeve 15 and terminal portion 16 is permissible within a full 90 degree axial displacement before the pin 17 is stopped by engagement with the stops 59 and 60.

The length of pin 17 is just slightly less than the diameter of the hollow interior portion 56. The pin 17 is inserted into hole 19 by first aligning hole 19 between the aligned holes 18, and then inserting the pin 17 through either hole 18 and fully through the hole 19 but not the other hole 18. The locking sleeve 15 is then moved longitudinally with respect to the stem 14 until the pin 17 is positioned against shoulder 57 and between the stops 59 and 60.

A pair of opposed holes 61 and 62 are provided through the locking sleeve 15, and a ball 63 is provided in each of the holes. The holes are swaged to loosely capture the balls and to hold them in place.

When the attachment cartridge 13 is assembled, the opposite ends of pin 17, projecting through corresponding opposite sides of hole 19, rest against shoulder 57. The pin 17 is thereby positioned to rotate 90 degrees between the stops 59 and 60. Shaft 51 is simultaneously positioned such that a circumference around the shaft in the proximity of the flat portions 52 is on line with the ball 63. Thus, as the locking sleeve 15 and connected terminal portion 16 are rotated with respect to the stem portion 14, the balls 63 are positioned either on the outer circumference of shaft 51 (FIG. 6), or in alignment with the flat portion 52 (FIG. 4).

With the stem 14 rotated as shown by FIG. 4, the balls 63 can be moved inwardly towards the flats 52 in response to longitudinal movement of the sleeve 15. With the stem 14 oriented as shown by FIG. 6, the balls 63 are urged into registration with the groove 64, as best seen in FIG. 5.

A bore hole 70 extends from the end 53, through the stem portion 14 to intercept an angled bore hole 71 that opens through the inclined surface 43 of the stem portion 14. The bore hole 71 exits the stem portion 14 between the "O"-rings 42 and 48. Another bore hole 72 extends from the end 53 at an angle through the stem portion 14 to exit at 75 through the front end 40 of the stem portion 14.

The terminal portion 16 of the attachment cartridge 13 includes the inlet bore holes 29 and 30. These bores extend through the full length of the terminal portion 16, and each includes an enlarged opening 78 and 79, respectively. Short rigid tube connectors 80 and 81 are inserted into the respective enlargements 78 and 79. Flexible plastic tubes 24 and 25 pass through finger grip 28, and are respectively inserted over the connectors 80 and 81, being secured in place by barbs 82 and 83, respectively (FIG. 2B). The other ends of the bore holes 29 and 30 terminate as "O"-ring recesses 87 and 88, respectively. Recess 87 receives an "O"-ring 89 and recess 88 receives an "O"-ring 90. The hole 21 extends diametrically through the terminal portion 16 between the bore holes 29 and 30, at the end adjacent to the "O"-rings 89 and 90.

In assembling the terminal portion 16 to the locking sleeve 15, the terminal portion is inserted to abut against the end 53 of the stem and the "O"-rings 89 and 90 are placed under a slight compression. The hole 21 is aligned with the holes 18 and the locking sleeve 15. The pin 20 is inserted through either hole 18, the bore hole 21 and the other hole 18 to secure the members together. The pin 20 then assures that the locking sleeve 15 will rotate with the terminal portion 16.

When the attachment cartridge is fully assembled, the locking sleeve 15 and terminal portion 16, are secured together by pin 20 and will rotate together through 90 degrees of axial displacement, with respect to the stem portion 14 and as limited by engagement of the pin 17 with stops 59 and 60. Also, the balls 63 are positioned in essentially the same transverse plane through the locking sleeve 15 and stem portion 14 as are the flat portions 52 of the stem portion. Thus, when the locking sleeve and terminal portion are fully rotated with respect to the stem, in a counterclockwise direction, as viewed from the left in FIGS. 2, 3 and 5, the balls 63 can move inwardly against the flat portions 52 of shaft 51. The fully assembled attachment cartridge 13, with the tubes 24 and 25 connected, is thus in a released condition so that it can be moved freely into and out of the head 11. If, however, after the attachment cartridge 13 has been fully inserted into the head 11, the locking sleeve and terminal portion are turned clockwise, the balls 63 are cammed outwardly of the locking sleeve by the shaft 51, and are moved partially into the groove 64 formed in the head 11. With the balls 63 extending into the groove 64, the attachment cartridge 13 is in a locked position and is securely held against withdrawal from the head 11.

When the attachment cartridge 13 is in its released position, the ports 29 and 30 through the terminal portion 16 are out of registry by 90 degrees with the outlet ports 70 and 72, respectively, through the stem 14. The locking cartridge can thus be inserted into the head 11 or removed therefrom without any attendant utility flow through the cartridge 13. When the attachment cartridge 13 is in its locked position, the ports 29 and 30 through the terminal portion are aligned with the outlet ports 70 and 72, respectively, through the stem 14. Water and air are then free to flow through the aligned ports and into ports 94 and 95 of the head 11. Utility flow through the syringe tip 96 is regulated by control valves 97 and 98 in the head 11.

It is presently preferred that water at 40 PSI be supplied to the cartridge 13 through tube 25 and that it flow through port 30, port 72, into chamber 99 of the head and through port 94 of the head. With the valve 97 closed, pressure in chamber 99 acts on the stem 14 to bias it out of the head. This bias force causes a binding action on the balls 63 which tends more securely to hold them in groove 64. Resistance to inadvertent turning of the locking sleeve and terminal portion, relative to the head 11, is thereby increased.

Air is supplied to the cartridge through tube 24 at 80 PSI and flows through port 29 and port 70 to a chamber 100 and port 95 in the head 11. With the valve 98 closed, the pressure in chamber 100 acts on the inclined surface 43 to push the cartridge 13 from the head 11. This action causes further binding of the balls 63 in the groove 64, and additionally helps to maintain the cartridge 13 securely in the head 11.

When it is desired to disconnect the syringe 10 from the tubes 24 and 25 it is only necessary for a user to grasp the handle 12 with one hand and to grasp and turn the tubes 24 and 25 in a counterclockwise direction, as viewed from the left in FIGS. 2, 3 and 5. This turning movement displaces the ports 29 and 30 out of registration with ports 70 and 72, relieves the pressures in chambers 99 and 100, positions the flat portions 52 to permit balls 63 to move into the locking sleeve 15 and to allow removal of the attachment cartridge 13 from the head 11 and handle 12.

It is significant that when the cartridge 13 is removed, substantially all of the outer surface of the assembled syringe 10 (FIG. 1) remains in an easily transportable subassembly. The handle 12, head 11 and tip 96 portions of the syringe are those portions exposed to surface contamination in a dental operatory, and are thus those portions most appropriately subjected to sterilization procedures. It is a simple matter to remove the cartridge 13 and to subject the remaining surface components to high temperature steam sterilization. There is no practical necessity for exposing the internal components of the cartridge 13 to the rigors of steam sterilization.

While a preferred embodiment has been herein disclosed, it should be understood that the present disclosure is made by way of example only and that variations to the invention are possible, without departing from the subject matter coming within the scope of the following claims, and a reasonable equivalence thereof.

What is claimed:

1. A dental syringe, comprising:
    a syringe head having air and water channels therethrough and a chamber therein to receive one end of a latching cartridge;
    a latching cartridge having inlet air and water ports and outlet air and water ports, said latching cartridge being lockable within said chamber in a position such that said outlet air and water ports are in respective communication with said air and water channels through the syringe head; and
    means for simultaneously moving said inlet air and water ports into registration with said outlet air and water ports while locking said latching cartridge in said syringe head chamber and for moving said inlet air and water ports out of registration with said outlet air and water ports while unlocking said latching cartridge from said syringe head chamber.

2. A syringe according to claim 1, further including a handle projecting from said syringe head and extending beyond said latching cartridge, wherein said latching cartridge is contained within said syringe head and handle.

3. In a dental syringe of the type including a head portion with controls for regulating the supply of utilities through a tip carried by said head portion; a handle portion extending from attachment to said head portion; and mechanisms connected between utility supply conduits and said head portion for conducting utilities through valves from said supply conduits to said tip, the improvement which comprises constructing and arranging said mechanisms in a cartridge which is removably installable substantially entirely within said handle and head portions, said cartridge including means for stopping flow of air and water utilities when said cartridge is removed from said handle and head portions, whereby said handle and head portions may be disconnected from said cartridge and supply conduits for sterilization.

4. An improvement according to claim 3, wherein said cartridge is constructed and arranged for quick disconnect association with said handle and head portions.

5. A dental syringe, comprising:
a syringe head having air and water channels therethrough and a chamber therein to receive one end of a latching cartridge;
a latching cartridge having inlet air and water pots and outlet air and water ports, said latching cartridge being lockable within said chamber in a position such that said outlet air and water ports are in respective communication with said air and water channels through the syringe head;
means for simultaneously moving said inlet air and water ports into registration with said outlet air and water ports while locking said latching cartridge in said syringe head chamber and for moving said inlet air and water ports out of registration with said outlet air and water ports while unlocking said latching cartridge from said syringe head chamber;
a handle projecting from said syringe head and extending beyond said latching cartridge, wherein said latching cartridge is contained within said syringe head and handle; and
a flexible finger grip having air and water supply tubes fitted tightly therethrough, said grip closing the end of the handle remote from the syringe head, and said air and water supply tubes being connected, respectively, to said air and water inlet ports of said cartridge.

6. A dental syringe, comprising:
a syringe head having air and water channels therethrough and a chamber therein to receive one end of a latching cartridge;
a latching cartridge having inlet air and water ports and outlet air and water ports, said latching cartridge being lockable within said chamber in a position such that said outlet air and water ports are in respective communication with said air and water channels through the syringe head;
means for simultaneously moving said inlet air and water ports into registration with said outlet air and water ports while locking said latching cartridge in said syringe head chamber and for moving said inlet air and water ports out of registration with said outlet air and water ports while unlocking said latching cartridge from said syringe head chamber;
wherein said latching cartridge comprises a stem portion, a locking sleeve and a terminal portion; said inlet air and water ports are through said terminal portion; said outlet air and water ports are through said stem portion, and said stem portion and said terminal portion are each coupled to said locking sleeve.

7. A syringe according to claim 6, further including a flexible finger grip having air and water supply tubes fitted tightly therethrough, said grip closing the end of the handle remote from the syringe head, and said air and water supply tubes being connected, respectively, to said air and water inlet ports of said cartridge.

8. A syringe according to claim 6, further including:
means to prevent axial rotation of said stem portion;
means limiting axial rotation of said locking sleeve and said terminal portion relative to said stem portion to move said inlet air and water ports through said terminal portion into and out of registration with said outlet air and water ports through said stem portion.

9. A syringe according to claim 8, further including a handle projecting from said syringe head and extending beyond said latching cartridge, wherein said latching cartridge is contained within said syringe head and handle.

10. A syringe according to claim 8, further including:
a compressible seal around one of said air ports between said terminal portion and said stem portion, and a compressible seal around one of between said terminal portion and said stem portion.

11. A syringe according to claim 10, further including a flexible finger grip having air and water supply tubes fitted tightly therethrough, said grip closing the end of the handle remote from the syringe head, and said air and water supply tubes being connected, respectively, to said air and water inlet ports of said cartridge.

12. A syringe according to claim 11, further including:
a plurality of balls carried by a wall of said locking sleeve, said balls being movable to extend outwardly of said locking sleeve and to extend into said locking sleeve, a flat portion corresponding to each ball being formed on a shaft of said stem portion, said shaft having an approximately circular cross-section; and
a groove around the interior of a boss of the syringe head, said balls, flat portions and groove being in essentially the same plane transverse to the longitudinal axis of the attachment cartridge when said cartridge is fully inserted into said syringe head chamber.

13. A syringe according to claim 12, wherein said stem portion is constructed and arranged so that when the inlet air and water ports are in registration with the outlet air and water ports, a circular portion of said shaft is adjacent said balls to move said balls into said grove, but when said inlet air and water ports are out of registration with said outlet air and water ports, said balls are adjacent said flat portion of said shaft so that they may be urged from said groove.

14. A syringe according to claim 8, wherein the means to prevent axial rotation of the stem portion comprises a distal drive head formed on said stem portion and a corresponding socket formed in said syringe head.

15. A syringe according to claim 14, further including a handle projecting from said syringe head and extending beyond said latching cartridge, wherein said latching cartridge is contained within said syringe head and handle.

16. A syringe according to claim 15, further including:
a compressible seal around one of said air ports between said terminal portion and said stem portion, and a compressible seal around one of said water ports between said terminal portion and said stem portion.

17. A syringe according to claim 16, further including a flexible finger grip having air and water supply tubes fitted tightly therethrough, said grip closing the end of the handle remote from the syringe head, and said air and water supply tubes being connected, respectively, to said air and water inlet ports of said cartridge.

18. A syringe according to claim 17, further including:
- a plurality of balls carried by a wall of said locking sleeve, said balls being movable to extend outwardly of said locking sleeve and to extend into said locking sleeve, a flat portion corresponding to each ball being formed on a shaft of said stem portion, said shaft having an approximately circular cross-section; and
- a groove around the interior of a boss of the syringe head, said balls, flat portions and groove being in essentially the same plane transverse to the longitudinal axis of the attachment cartridge when said cartridge is fully inserted into said syringe head chamber.

19. A syringe according to claim 18, wherein said stem portion is constructed and arranged so that when the inlet air and water ports are in registration with the outlet air and water ports, a circular portion of said shaft is adjacent said balls to move said balls into said grove, but when said inlet air and water ports are out of registration with said outlet air and water ports, said balls are adjacent said flat portion of said shaft so that they may be urged from said groove.

20. In a dental syringe of the type including a head portion with controls for regulating the supply of utilities through a tip carried by said head portion; a handle portion extending from attachment to said head portion; and mechanisms connected between utility supply conduits and said head portion for conducting utilities through valves from said supply conduits to said tip, the improvement which comprises constructing and arranging said mechanisms in a cartridge which is removably installable substantially entirely within said handle and head portions, whereby said handle and head portions may be disconnected from said cartridge and supply conduits for sterilization; wherein said cartridge is constructed and arranged for quick disconnect association with said handle and head portion, and wherein said syringe head includes air and water channels therethrough and a chamber therein to receive one end of said cartridge; said cartridge has inlet air and water ports and outlet air and water ports, and is lockable within said chamber in a position such that said outlet air and water ports are in respective communication with said air and water channels through said syringe head; and said cartridge further includes means for simultaneously moving said inlet air and water ports into registration with said outlet air and water ports while locking said cartridge in said syringe head chamber and for moving said inlet air and water ports out of registration with said outlet air and water ports while unlocking said cartridge from said syringe head chamber.

21. An improvement according to claim 20, wherein said cartridge comprises a stem portion, a locking sleeve and a terminal portion; said inlet air and water ports are through said terminal portion; said outlet air and water ports are through said stem portion, and said stem portion and said terminal portion are each coupled to said locking sleeve.

22. An improvement according to claim 21, further including a flexible finger grip having air and water supply tubes fitted tightly therethrough, said grip closing the end of said handle portion remote from said head portion, and said air and water supply tubes being connected, respectively, to said air and water inlet ports of said cartridge.

23. An improvement according to claim 22, further including means to prevent axial rotation of said stem portion; and means limiting axial rotation of said locking sleeve and said terminal portion relative to said stem portion to move said inlet air and water ports through said terminal portion into and out of registration with said outlet air and water ports through said stem portion.

24. An improvement according to claim 23 wherein said handle projects from said syringe head and extends beyond said cartridge, whereby said latching cartridge is contained within said syringe head and handle.

* * * * *